(12) United States Patent
Schwitter et al.

(10) Patent No.: US 10,227,298 B2
(45) Date of Patent: *Mar. 12, 2019

(54) SOLID FORMS OF A PHARMACEUTICALLY ACTIVE COMPOUND

(71) Applicant: Hoffmann-La Roche Inc., Nutley, NJ (US)

(72) Inventors: Urs Schwitter, Reinach (CH); Ralph Diodone, Breisach (DE); Rudolf Benz, Appenzell/Steinegg (CH); Zhongjiang Jia, Kennett Square, PA (US); Choi Duk Soon, Flanders, NJ (US); Ningxin Yan, Chandler, AZ (US); Bharat Patel, Piscataway, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/303,792

(22) PCT Filed: Apr. 13, 2015

(86) PCT No.: PCT/EP2015/057937
§ 371 (c)(1),
(2) Date: Oct. 13, 2016

(87) PCT Pub. No.: WO2015/158648
PCT Pub. Date: Oct. 22, 2015

(65) Prior Publication Data
US 2017/0037005 A1  Feb. 9, 2017

Related U.S. Application Data

(60) Provisional application No. 61/979,649, filed on Apr. 15, 2014.

(51) Int. Cl.
C07D 207/16 (2006.01)
A61K 31/40 (2006.01)
C07D 207/10 (2006.01)

(52) U.S. Cl.
CPC ........... C07D 207/16 (2013.01); A61K 31/40 (2013.01); C07D 207/10 (2013.01); C07B 2200/13 (2013.01)

(58) Field of Classification Search
CPC .................................................. C07D 207/16
See application file for complete search history.

(56) References Cited

U.S. PATENT DOCUMENTS

| | | | | |
|---|---|---|---|---|
| 8,354,444 B2 * | 1/2013 | Bartkovitz | ........... | C07D 207/16 514/408 |
| 9,216,170 B2 * | 12/2015 | Higgins | ............... | A61K 31/437 |
| 9,371,280 B2 * | 6/2016 | Bartkovitz | ........... | C07D 471/04 |
| 9,427,427 B2 * | 8/2016 | Lomuscio | ............... | A61K 31/40 |

FOREIGN PATENT DOCUMENTS

| | | |
|---|---|---|
| WO | 2011098398 A1 | 8/2011 |
| WO | 2013139687 A1 | 9/2013 |
| WO | 2014114575 A1 | 7/2014 |
| WO | WO 2014/128094 A1 | 8/2014 |

OTHER PUBLICATIONS

Bartkovitz et al (2011): STN International HCAPLUS database, (Columbus, Ohio), Accession No. 2011:1031398.*
The English translation of the Japanese Office Action, dated Oct. 17, 2017, in the related Japanese patent application No. 2016-562779.
The Singapore Search Report and Written Opinion, dated Nov. 14, 2017, in the related Singapore application No. 11201608559Q.
Yuusaku Shioji, Manufacture Technology of Solid Tablet, Tokyo: CMC Publishing Co., Ltd., Jan. 27, 2003, pp. 9, 12, 13, ISBN 4-88231-783-4.
Kazuhide Serizawa, The Science of Polymorphism and Crystallization of Medicaments, 2002, pp. 273, 278, 305-317.
Noriaki Hirayama, Editor, Organic Compound Crystal Formulation Handbook: Principles and Knowhow, Maruzen Publishing Co., Ltd., Jul. 25, 2008, pp. 57-84.
The International Search Report and Written Opinion, dated Jul. 27, 2015, in the related PCT Application No. PCT/EP2015/057937.
The English translation of the Chinese Office Action, dated Jul. 31, 2018, in the related Chinese patent application No. 201580019543.0.

* cited by examiner

*Primary Examiner* — Golam M Shameem (57) ABSTRACT

The present application discloses solid forms of compound (1) (1), methods for making them, as well as compositions comprising said solid forms.

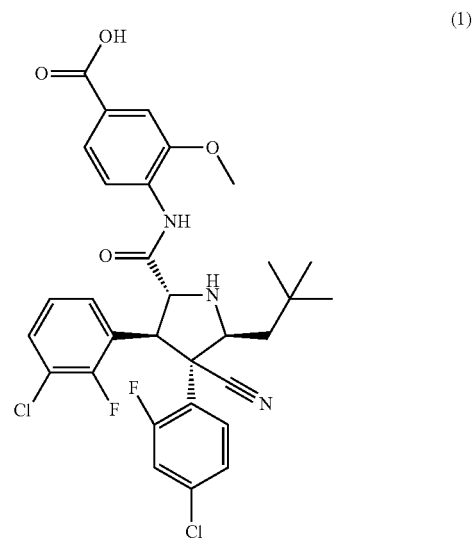

(1)

12 Claims, 15 Drawing Sheets

SOLID FORMS OF A PHARMACEUTICALLY ACTIVE COMPOUND

CROSS-REFERENCE TO RELATED APPLICATIONS

This application is a National Stage Application of PCT/EP2015/057937 filed Apr. 13, 2015, which claims priority from U.S. Provisional Patent Application No. 61/979,649 filed on Apr. 15, 2014. Each of the prior mentioned applications is hereby incorporated by reference herein in its entirety.

FIELD OF THE INVENTION

The present invention relates to various forms of compounds, for example, compounds that have use in pharmaceutical applications.

BACKGROUND OF THE INVENTION

The compound 4-{[(2R, 3S,4R,5S)-4-(4-Chloro-2-Fluoro-Phenyl)-3-(3-Chloro-2-Fluoro-Phenyl)-4-Cyano-5-(2,2-Dimethyl-Propyl)-Pyrrolidine-2-Carbonyl]-Amino}-3-Methoxy-Benzoic Acid is represented by formula (1)

(1)

The compound of formula (1), or compound (1), as well as methods for making it, are disclosed in U.S. Pat. No. 8,354,444 and WO2011/098398.

4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid ($C_{31}H_{29}Cl_2F_2N_3O_4$) is a potent and selective inhibitor of the p53-MDM2 interaction that activates the p53 pathway and induces cell cycle arrest and/or apoptosis in a variety of tumor types expressing wild-type p53 in vitro and in vivo. Compound (1) belongs to a novel class of MDM2 inhibitors having potent anti-cancer therapeutic activity, in particular in leukemia such as acute myeloid leukemia (AML) and solid tumors such as for example head and neck, non-small cell lung, breast and colorectal cancers, as well as sarcoma.

The above-identified international patent application and US Patent describe Compound A in crystalline form and is herein incorporated by reference in its totality. The crystalline form of the compound has an on-set melting point of approximately 277° C. The crystalline forms have relatively low aqueous solubility (<0.05 µg/mL in water) at physiological pHs (which range from pH1.5-8.0) and consequently less than optimal bioavailability (high variability). It is thus desirable to obtain a form of the compound which has improved solubility/dissolution rate and bioavailability.

Active pharmaceutical ingredients (API's) may be prepared in a variety of different forms, such as for example salts, solvates, hydrates, co-crystals. API's may also be in their amorphous state or one or several crystalline forms (polymorphs). Depending on the form, the physicochemical properties of an API may change, leading to e.g. different solubility, thermodynamic stability, density or melting point of different forms. Such physicochemical properties therefore may have significant influence of the efficacy or bioavailability of a known API.

SUMMARY OF THE INVENTION

The present invention provides solid forms of compound (1) selected from the group consisting of,
 a) a substantially amorphous form of compound (1);
 b) a hemi-hydrate, hydrate, hemi-solvate or solvate of compound (1);
 c) a polymorph of compound (1); or
 d) a pharmaceutically acceptable salt of compound (1).

In one particular embodiment, said solid form is selected from a hemi-hydrate or -solvate designated form IV, V, VI, VII of compound (1).

In another particularly preferred embodiment, said solid form is selected from a polymorph designated form I, II and III of compound (1).

In yet another preferred embodiment, said solid form is selected from the substantially amorphous form of compound (1).

In another embodiment, the invention provides a method of for treating a disease or condition in a mammal in need thereof. The method includes administering to the mammal an effective amount of a composition comprising a solid form compound as described herein.

The solid forms disclosed herein may be further processed into any type of solid pharmaceutical preparations or dosage forms, which are known to the person of skill in the art. Particularly preferred are oral dosage forms such as tablets, capsules, pills, powders, suspensions, pasts and the like. Detailed descriptions of suitable excipients as well as methods for making such pharmaceutical preparations can for example be found in: Raymond C. Rowe et al, *Handbook of Pharmaceutical Excipients, 6$^{th}$ edition*, 2009, Pharmaceutical Press (Publ.); ISBN-10: 0853697922.

Consequently, so obtained pharmaceutical preparations form further embodiments provided herein.

DETAILED DESCRIPTION OF THE INVENTION

As used herein, the general term "amorphous forms" denote a material that lacks long range order and as such does not show sharp X-ray peaks. The X-Ray Powder Diffraction (XRPD) pattern of an amorphous material is characterized by one or more amorphous halos. More specifically, the term "amorphous form" as used herein refers to the amorphous form of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (compound 1) as such, provided said amorphous form does not form a one phase system, such as for example a solid dispersion or microprecipitated bulk powder (MBP) together with any type of supporting material such as polymers or the like.

The amorphous form of the invention is preferentially substantially pure, meaning the amorphous form includes less than about 15%, preferably less than about 10%, preferably less than about 5%, preferably less than about 1%, even more preferably less than 0.1% by weight of impurities, including other polymorph forms of compound (1). In some embodiments, at least about 30-99% by weight of the total of compound 1 in the composition is present as the amorphous form. In further embodiments, at least about 70%, at least about 80%, at least about 90%, at least about 99% or at least about 99.9% by weight of the total of compound 1 in the composition is present as the amorphous form. Also provided by the invention are compositions consisting essentially of compound (1) wherein at least about 97-99% by weight of the compound (1) is present in the composition as an amorphous form, a polymorph form, a solvate form as described herein or combinations thereof.

The term "polymorph" as used herein means one of the different crystal structures in which a compound can crystallize. Polymorphs are best characterized by their space group and unit-cell parameters. This term is reserved for materials with the same elemental analysis.

"Ambient temperature" means any temperature in the range of 18 to 28° C., preferably 20 to 24° C.

The term "composition" refers to a pharmaceutical preparation suitable for administration to an intended animal subject for therapeutic purposes that contains at least one pharmaceutically active compound, including any solid form thereof. The composition may include at least one additional pharmaceutically acceptable component to provide an improved formulation of the compound, such as a suitable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

FTIR (Fourier-Transform Infrared) spectra were recorded as film of a Nujol suspension of approximately 5 mg of sample and few Nujol between two sodium chloride plates, with an FTIR spectrometer in transmittance. The Spectrometer is a Nicolet™ 20SXB or equivalent (resolution 2 cm-1, 32 or more co-added scans, MCT detector). Characteristic wavenumbers for the solid forms according to the present invention are shown in Table 1 below:

TABLE 1

Characteristic Bands (cm$^{-1}$) in the IR Spectra for amorphous, polymorphs and solvates of Compound (1). (Error on wavenumbers is ±1 cm$^{-1}$)

| Form Amorphous | Form I | Form II | Form III | Form IV | Form V | Form VI | Form VII |
|---|---|---|---|---|---|---|---|
| 1705 | 1703 | n.d. | 1687 | 1718 | 1684 | 1707 | 1752 |
| 1687 | 1688 | n.d. | 1599 | 1684 | 1588 | 1687 | 1702 |
| 1600 | 1599 | n.d. | 1586 | 1586 | 1524 | 1601 | 1652 |
| 1587 | 1588 | n.d. | 1524 | 1525 | 1484 | 1588 | 1591 |
| 1525 | 1525 | n.d. | 1482 | 1485 | 1458 | 1525 | 1531 |
| 1483 | 1484 | n.d. | 1457 | 1467 | 1406 | 1483 | 1492 |
| 1409 | 1408 | n.d. | 1408 | 1457 | 1273 | 1425 | 1460 |
| 1367 | 1368 | n.d. | 1344 | 1407 | 1247 | 1408 | 1419 |
| 1343 | 1342 | n.d. | 1274 | 1294 | 1229 | 1367 | 1266 |
| 1299 | 1297 | n.d. | 1249 | 1273 | 1176 | 1343 | 1221 |
| 1276 | 1274 | n.d. | 1221 | 1230 | 1128 | 1302 | 1179 |
| 1250 | 1248 | n.d. | 1178 | 1221 | 1086 | 1276 | 1114 |
| 1230 | 1230 | n.d. | 1126 | 1178 | 1029 | 1232 | 1031 |
| 1221 | 1130 | n.d. | 1084 | 1128 | 901 | 1221 | 899 |
| 1178 | 1035 | n.d. | 1031 | 1085 | 887 | 1086 | 884 |
| 1128 | 903 | n.d. | 901 | 1032 | 856 | 884 | 861 |
| 1086 | 886 | n.d. | 883 | 900 | 817 | 766 | 816 |
| 1034 | 764 | n.d. | 856 | 883 | 779 | 759 | 779 |
| 902 | — | n.d. | 846 | 856 | 763 | — | 768 |
| 885 | — | n.d. | 816 | 817 | 729 | — | 746 |
| 817 | — | n.d. | 777 | 777 | 706 | — | 731 |
| 778 | — | n.d. | 756 | 763 | 661 | — | 709 |
| 765 | — | n.d. | 731 | 729 | — | — | 663 |
| 729 | — | n.d. | 703 | 704 | — | — | — |
| — | — | n.d. | 661 | 661 | — | — | — | n.d.: not determined

X-ray powder diffraction (XRPD) patterns were recorded at ambient conditions in transmission geometry with a STOE STADIP diffractometer (Cu K.radiation, primary monochromator, silicon strip detector, angular range 3° to 42° 2 Theta, approximately 30 minutes total measurement time). The samples were prepared and analyzed without further processing (e.g. grinding or sieving) of the substance. Characteristic 2-theta values for the solid forms according to the present invention are shown in Table 2 below:

TABLE 2

Distinguishing Characteristic 2-θ (2-theta) values in the XRPD pattern for amorphous, polymorphs and solvates of Compound (1)

| Form Amorphous | Form I | Form II | Form III | Form IV | Form V | Form VI | Form VII |
|---|---|---|---|---|---|---|---|
| — | 4.9 | 4.1 | 5.9 | 5.1 | 3.9 | 5.5 | 6.6 |
| — | 6.9 | 5.0 | 8.3 | 8.0 | 7.8 | 7.4 | 10.7 |
| — | 7.7 | 5.7 | 9.5 | 8.3 | 8.7 | 14.5 | 14.6 |
| — | 9.1 | 6.3 | 10.1 | 8.8 | 9.1 | 14.8 | 15.7 |
| — | 10.9 | 6.9 | 11.3 | 9.3 | 13.7 | 15.6 | 16.0 |
| — | 13.5 | 7.9 | 14.2 | 10.0 | 14.5 | 16.9 | 16.4 |
| — | 14.5 | 8.1 | 15.8 | 10.3 | 18.2 | 17.8 | 18.9 |
| — | 17.2 | 9.0 | 17.6 | 13.7 | 20.3 | 18.6 | 19.8 |
| — | 20.4 | 10.0 | 19.0 | 14.3 | — | 19.9 | 21.4 |
| — | 22.3 | 14.3 | 19.4 | 18.7 | — | 20.5 | 22.0 |
| — | 25.5 | 19.5 | 19.8 | 20.2 | — | 24.8 | 25.3 |
| — | — | — | 20.3 | 20.8 | — | 26.7 | 26.1 |
| — | — | — | 25.5 | 27.6 | — | — | — |

Figure 2:
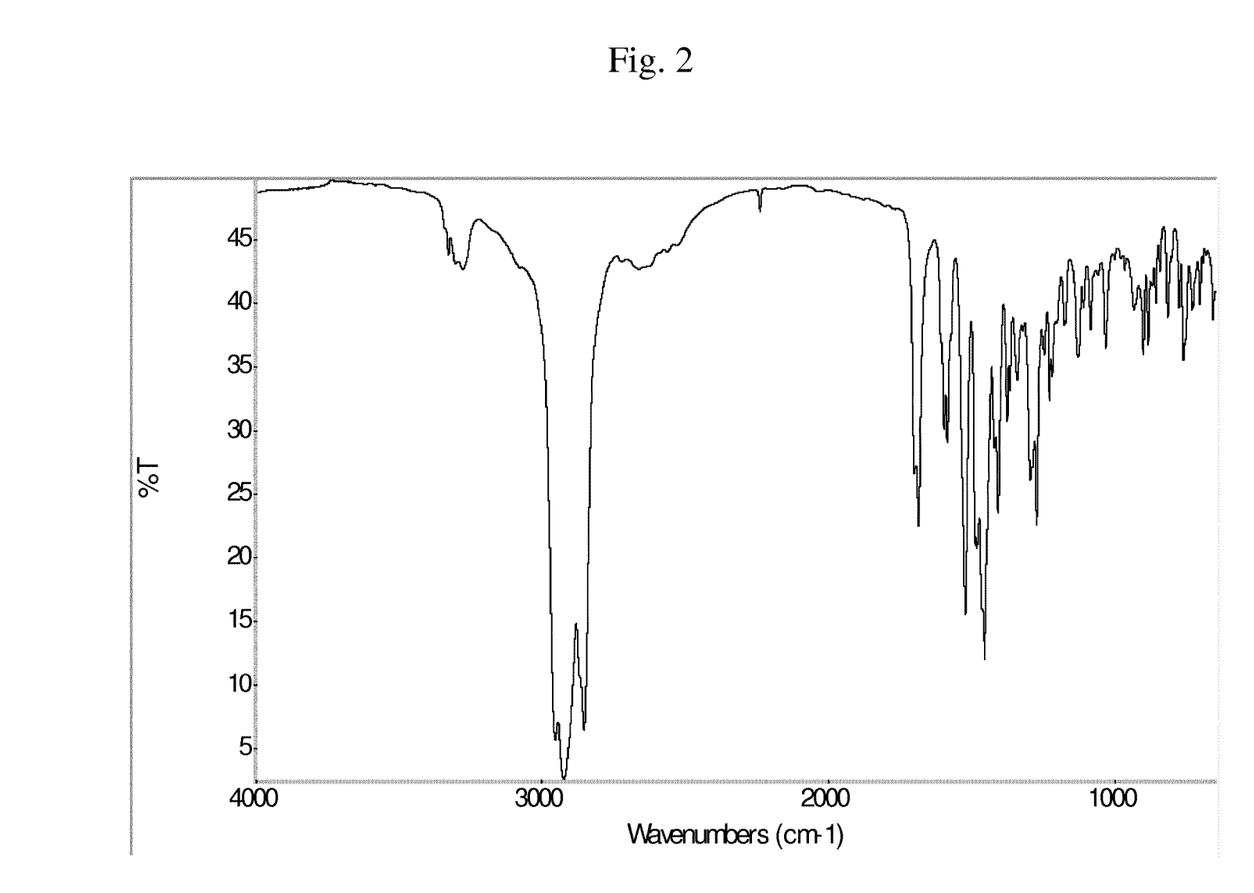
FIG. 2: FTIR spectra of Form I of compound (1)
Figure 8:
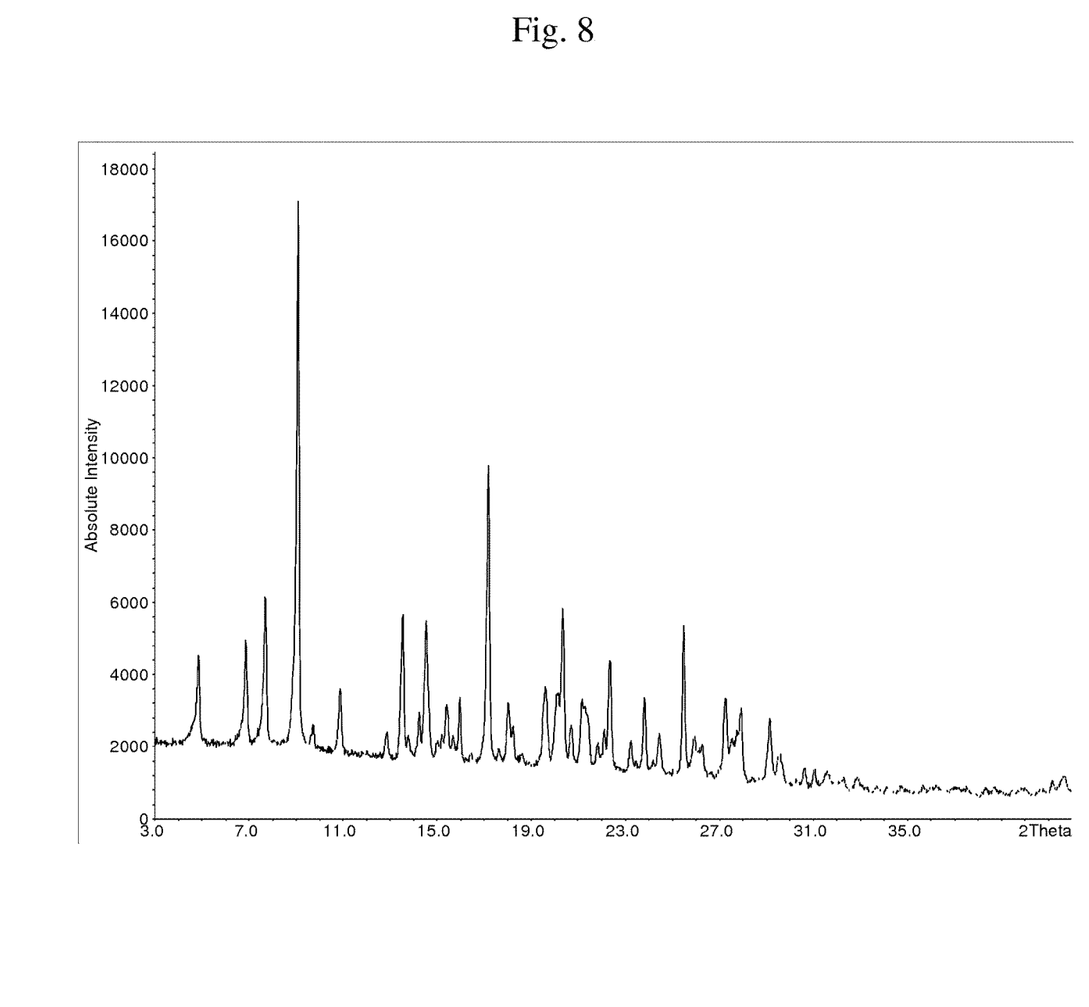
FIG. 8: XRPD curve of Form I of compound (1)

Therefore, in one embodiment there is provided the form I of compound (1), characterized by the XRPD patterns at 2-theta values of 4.9, 6.9, 7.7, 9.1, 10.9, 13.5, 14.5, 17.2, 20.4, 22.3 and 25.5; or by the corresponding characteristic wavenumbers according to Table 1.

Figure 9:
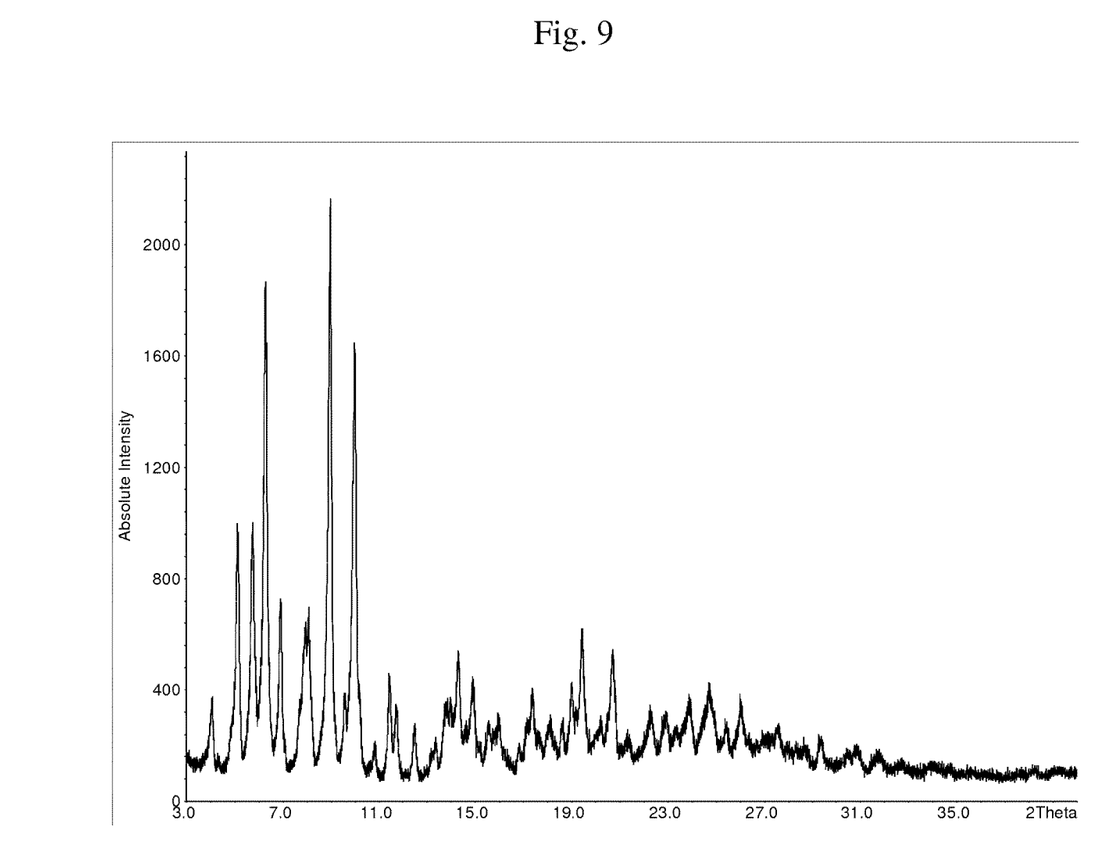
FIG. 9: XRPD curve of Form II of compound (1)

In another embodiment there is provided the form II of compound (1), characterized by the XRPD patterns at 2-theta values of 4.1, 5.0, 5.7, 6.3, 6.9, 7.9, 8.1, 9.0, 10.0, 14.3 and 19.5; or by the corresponding characteristic wavenumbers according to Table 1.

Figure 3:
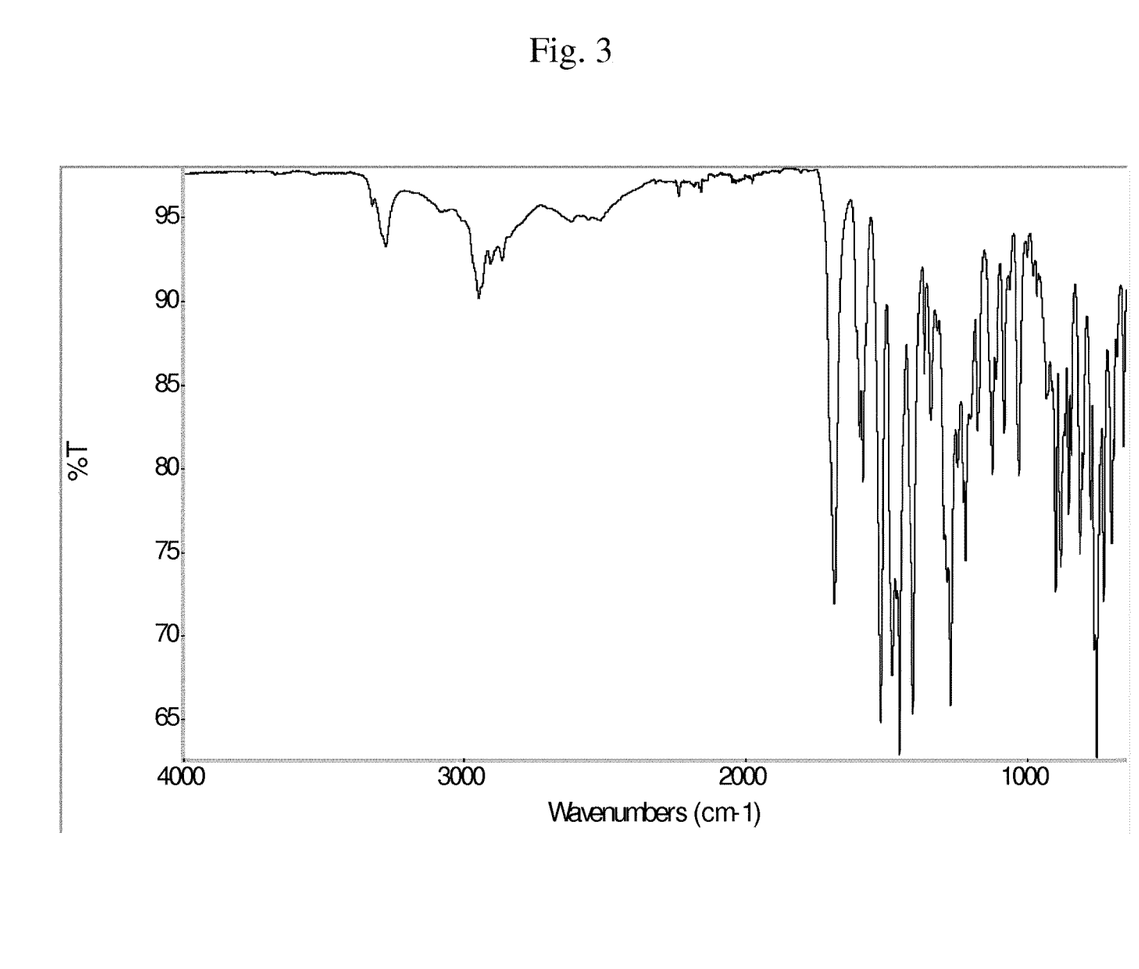
FIG. 3: FTIR spectra of Form III of compound (1)
Figure 10:
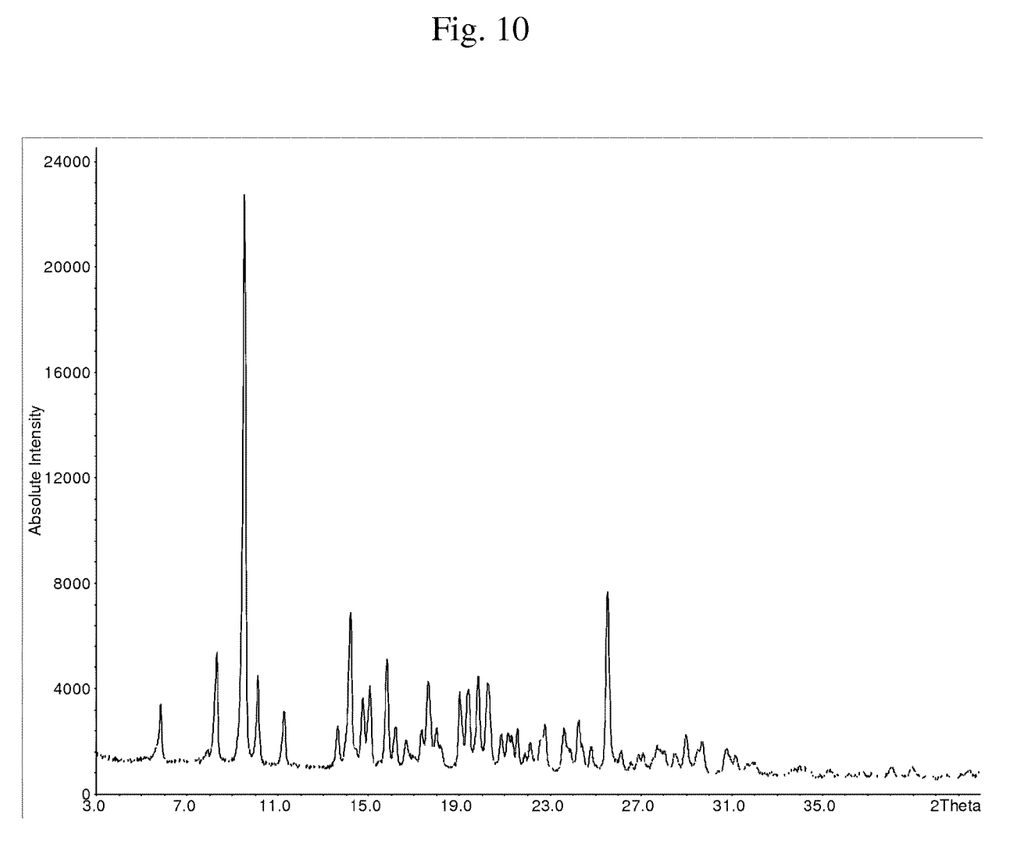
FIG. 10: XRPD curve of Form III of compound (1)

In another embodiment there is provided the form III of compound (1), characterized by the XRPD patterns at 2-theta values of 5.9, 8.3, 9.5, 10.1, 11.3, 14.2, 15.8, 17.6, 19.0, 19.4, 19.8, 20.3 and 25.5; or by the corresponding characteristic wavenumbers according to Table 1.

Figure 4:
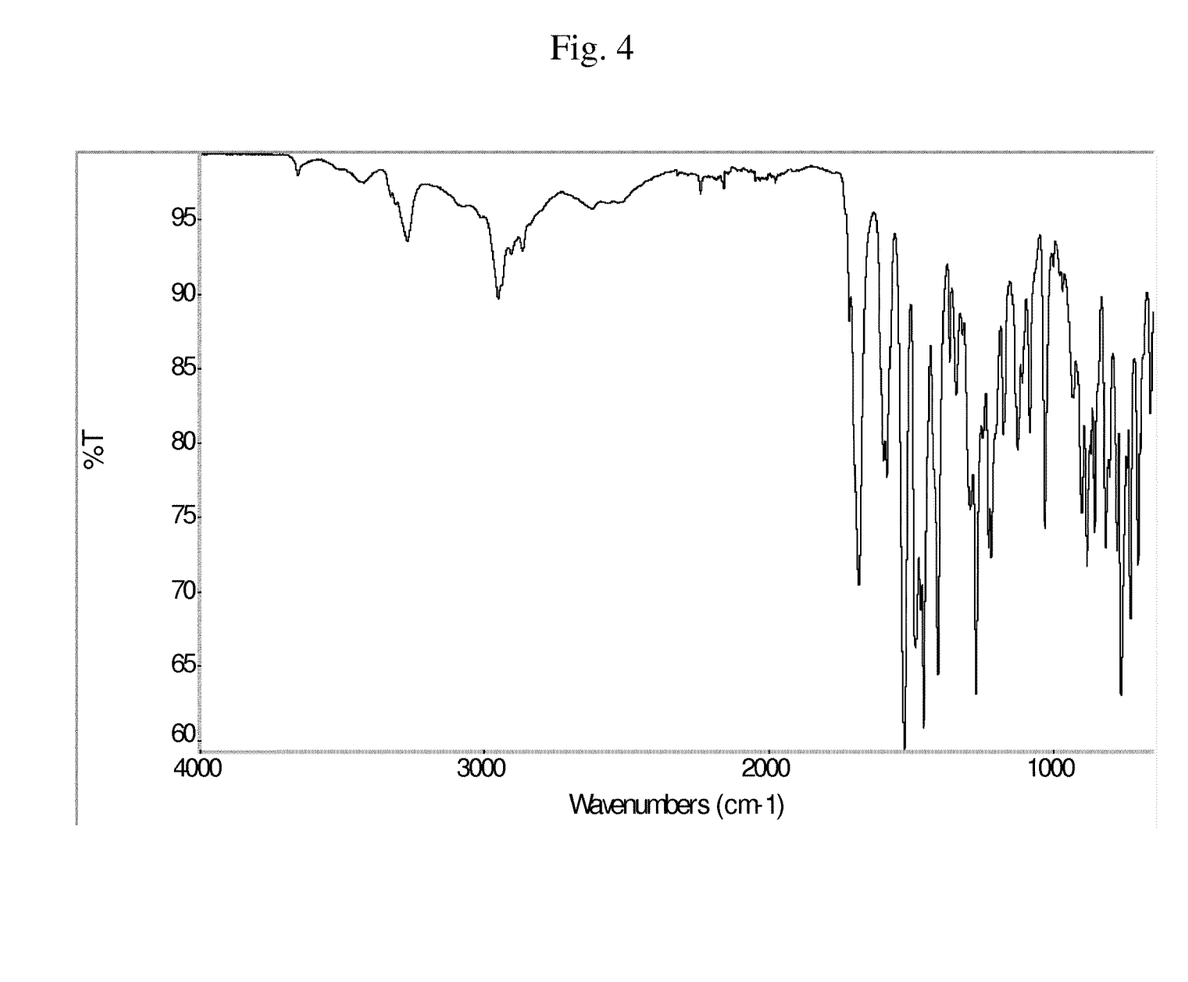
FIG. 4: FTIR spectra of Form IV of compound (1)
Figure 11:
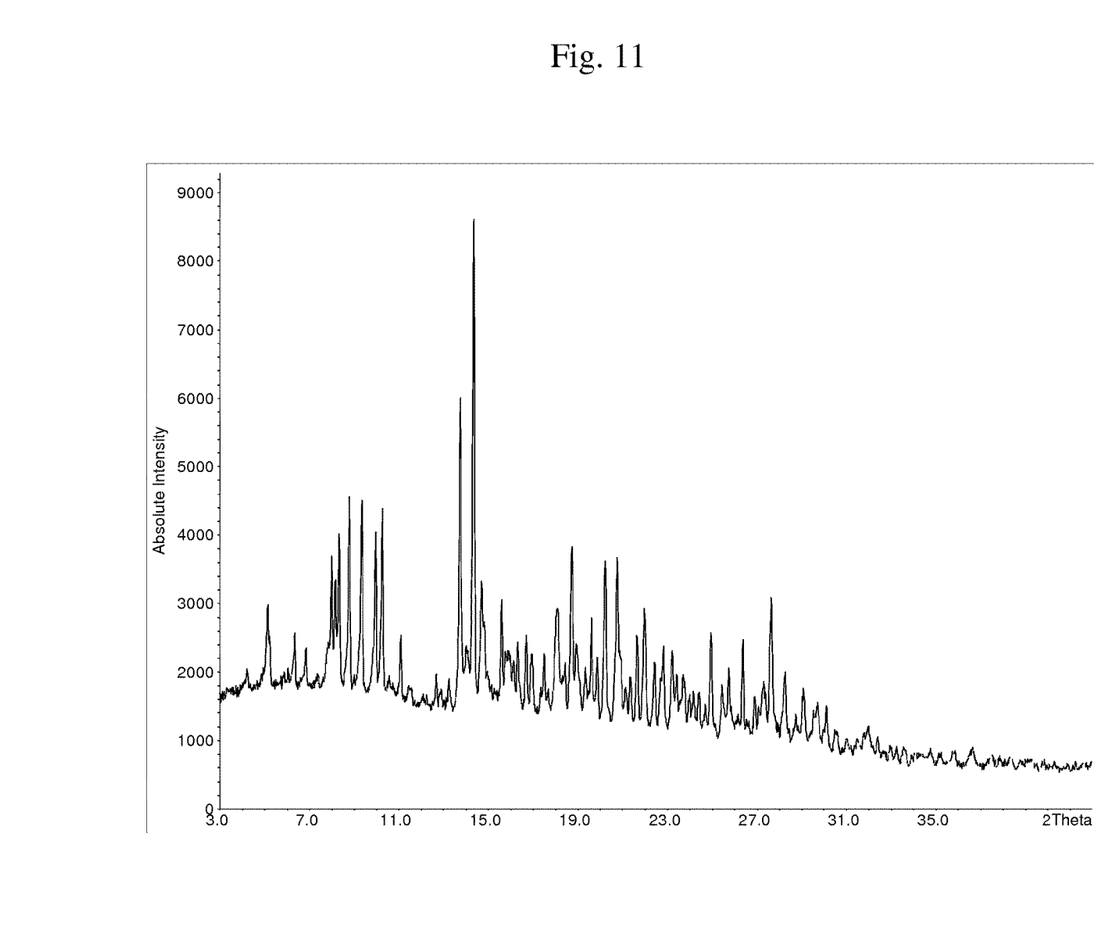
FIG. 11: XRPD curve of Form IV of compound (1)

In another embodiment there is provided the form IV of compound (1), characterized by the XRPD patterns at 2-theta values of 5.1, 8.0, 8.3, 8.8, 9.3, 10.0, 10.3, 13.7, 14.3, 18.7, 20.2, 20.8 and 27.6; or by the corresponding characteristic wavenumbers according to Table 1.

Figure 5:
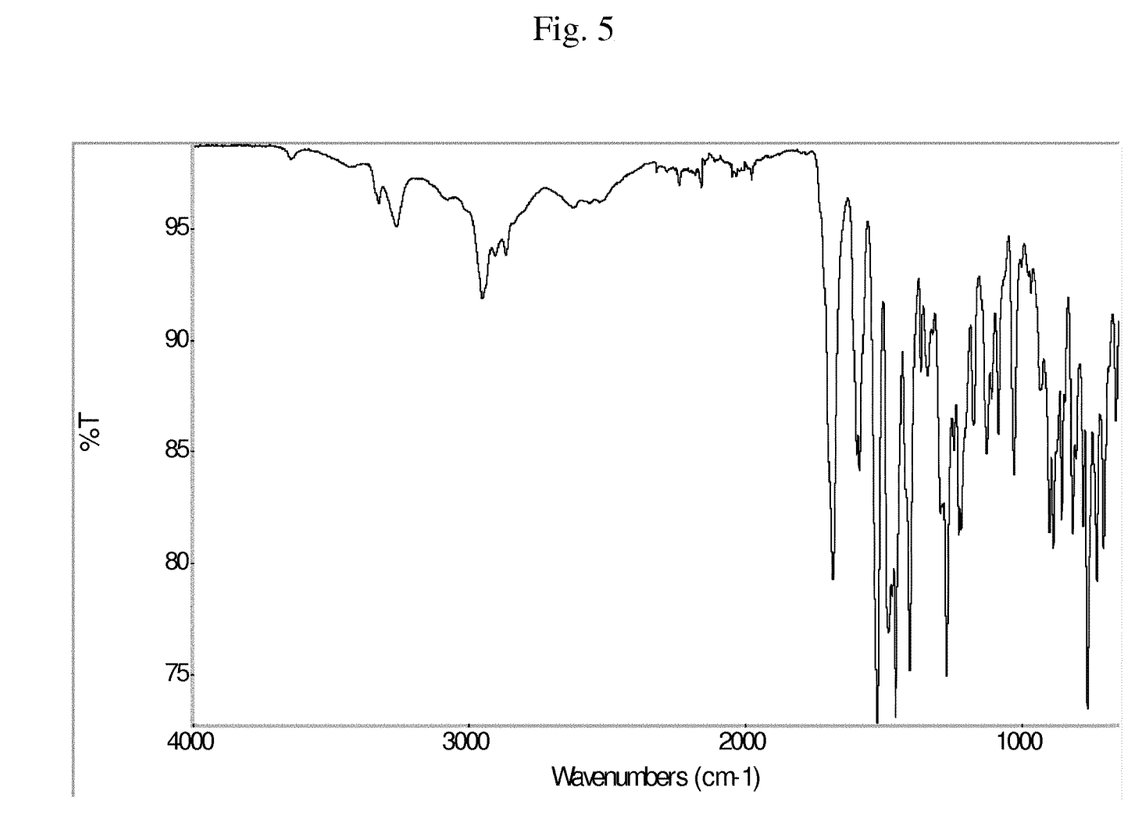
FIG. 5: FTIR spectra of Form V of compound (1)
Figure 12:
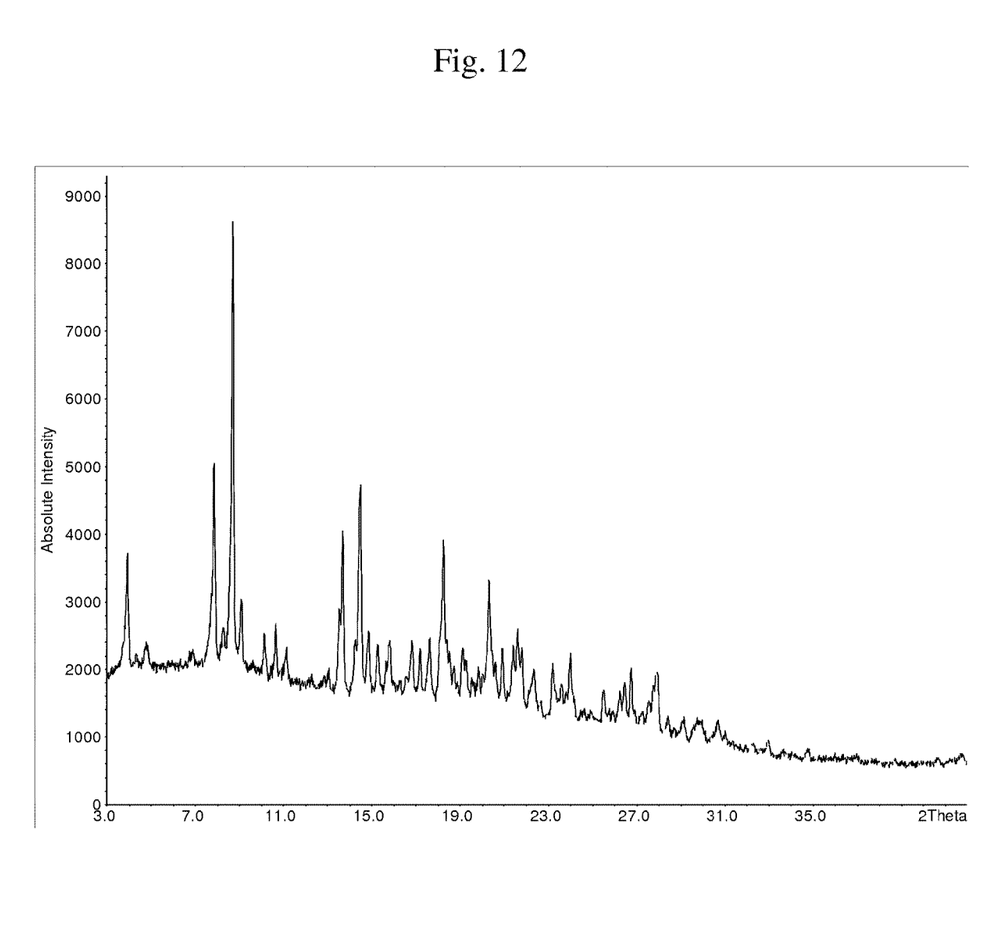
FIG. 12: XRPD curve of Form V of compound (1)

In another embodiment there is provided the form V of compound (1), characterized by the XRPD patterns at 2-theta values of 3.9, 7.8, 8.7, 9.1, 13.7, 14.5, 18.2 and 20.3; or by the corresponding characteristic wavenumbers according to Table 1.

Figure 6:
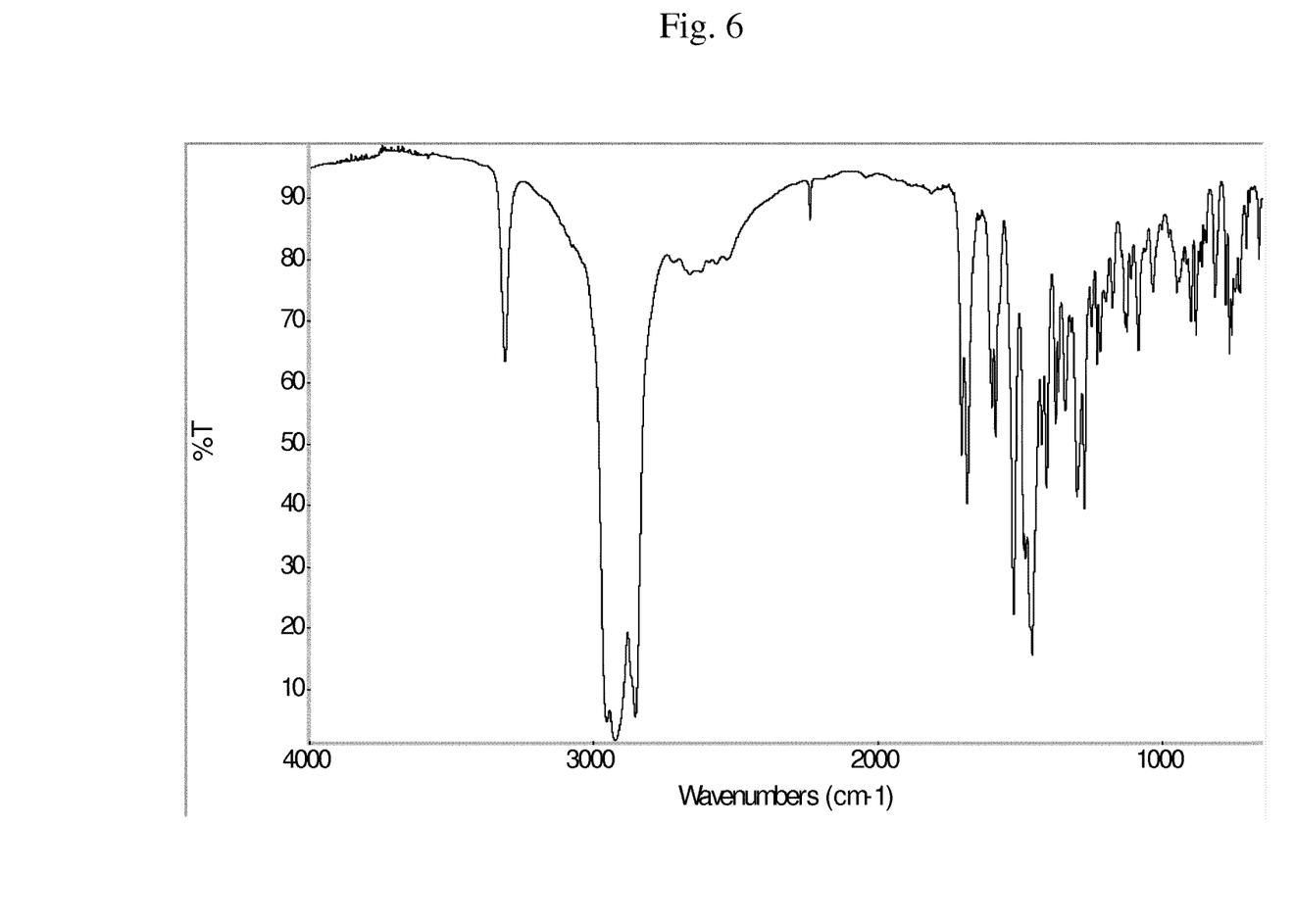
FIG. 6: FTIR spectra of Form VI of compound (1)
Figure 13:
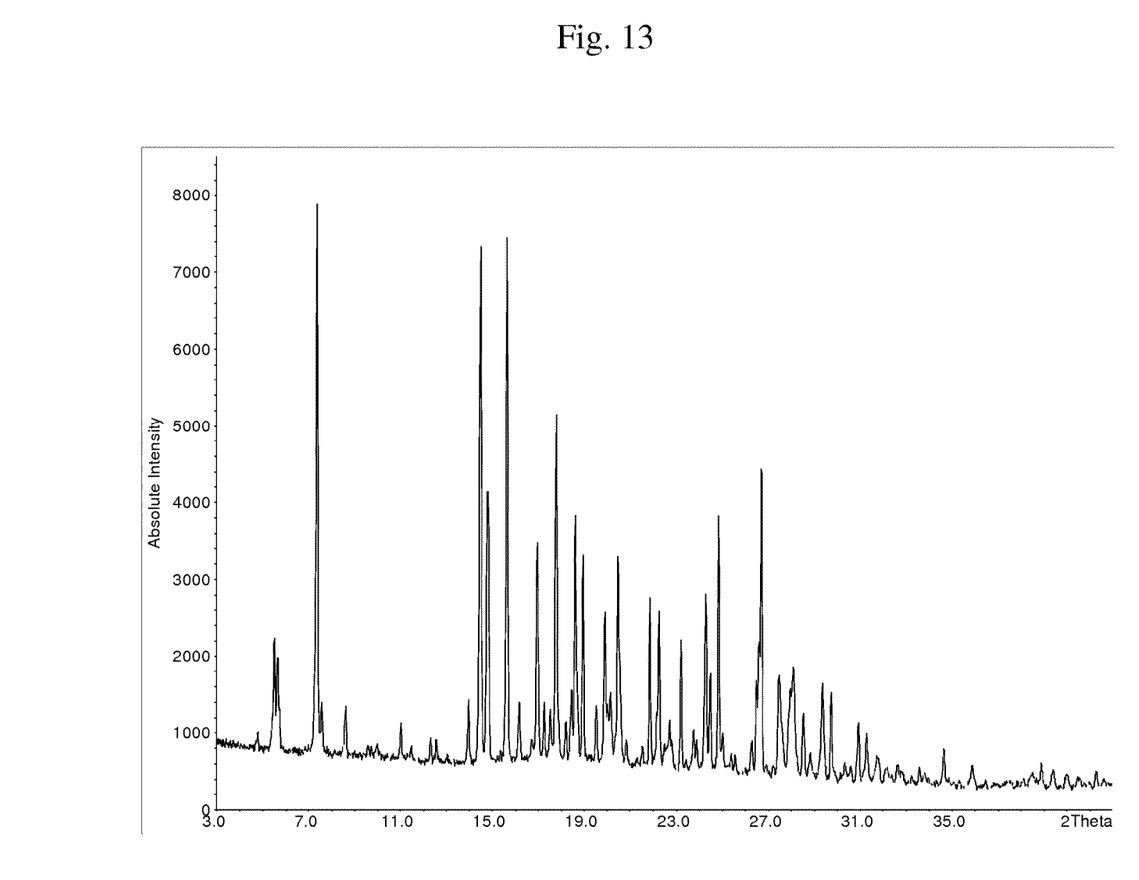
FIG. 13: XRPD curve of Form VI of compound (1)

In another embodiment there is provided the form VI of compound (1), characterized by the XRPD patterns at 2-theta values of 5.5, 7.4, 14.5, 14.8, 15.6, 16.9, 17.8, 18.6, 19.9, 20.5, 24.8 and 26.7; or by the corresponding characteristic wavenumbers according to Table 1.

Figure 7:
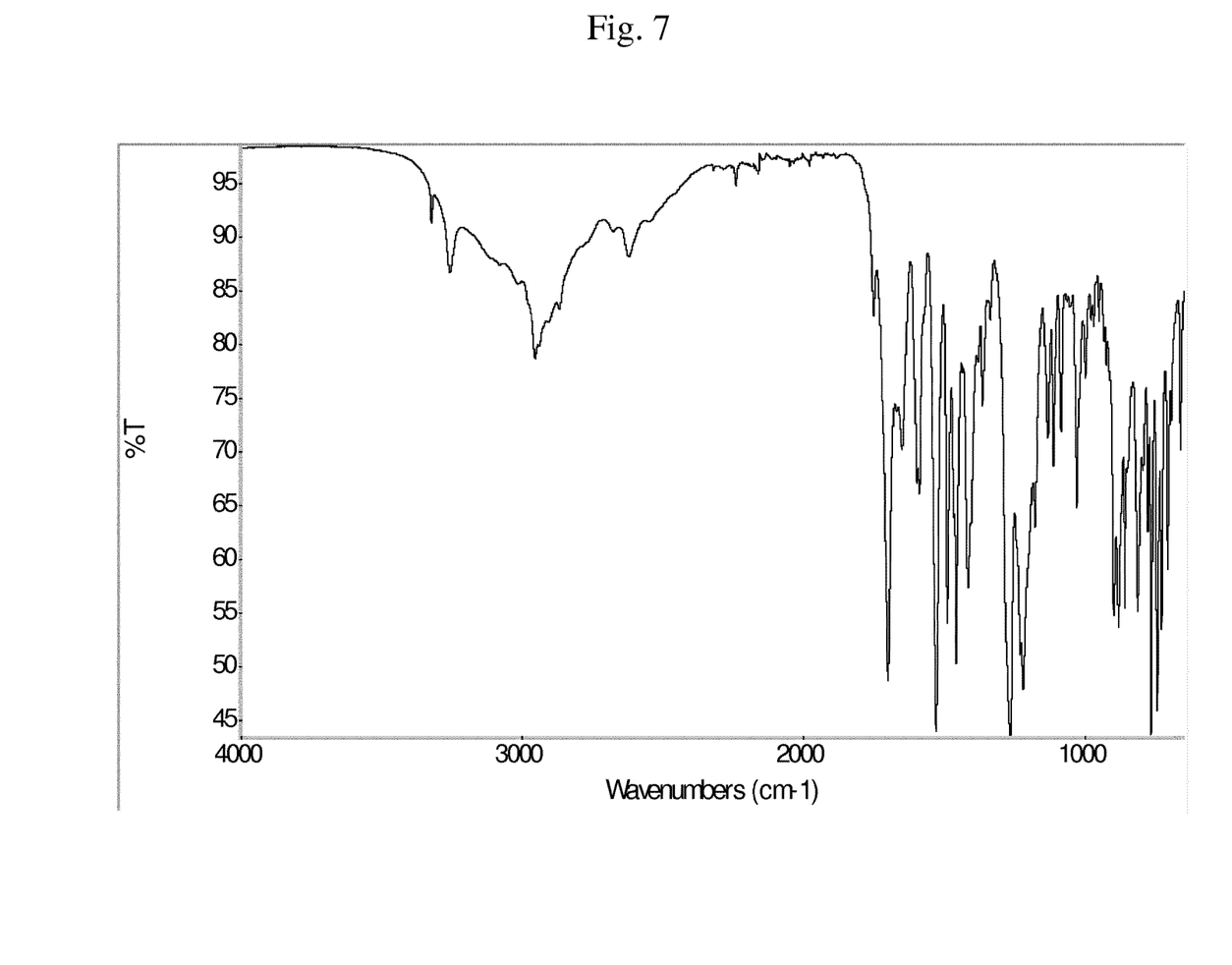
FIG. 7: FTIR spectra of Form VII of compound (1)
Figure 14:
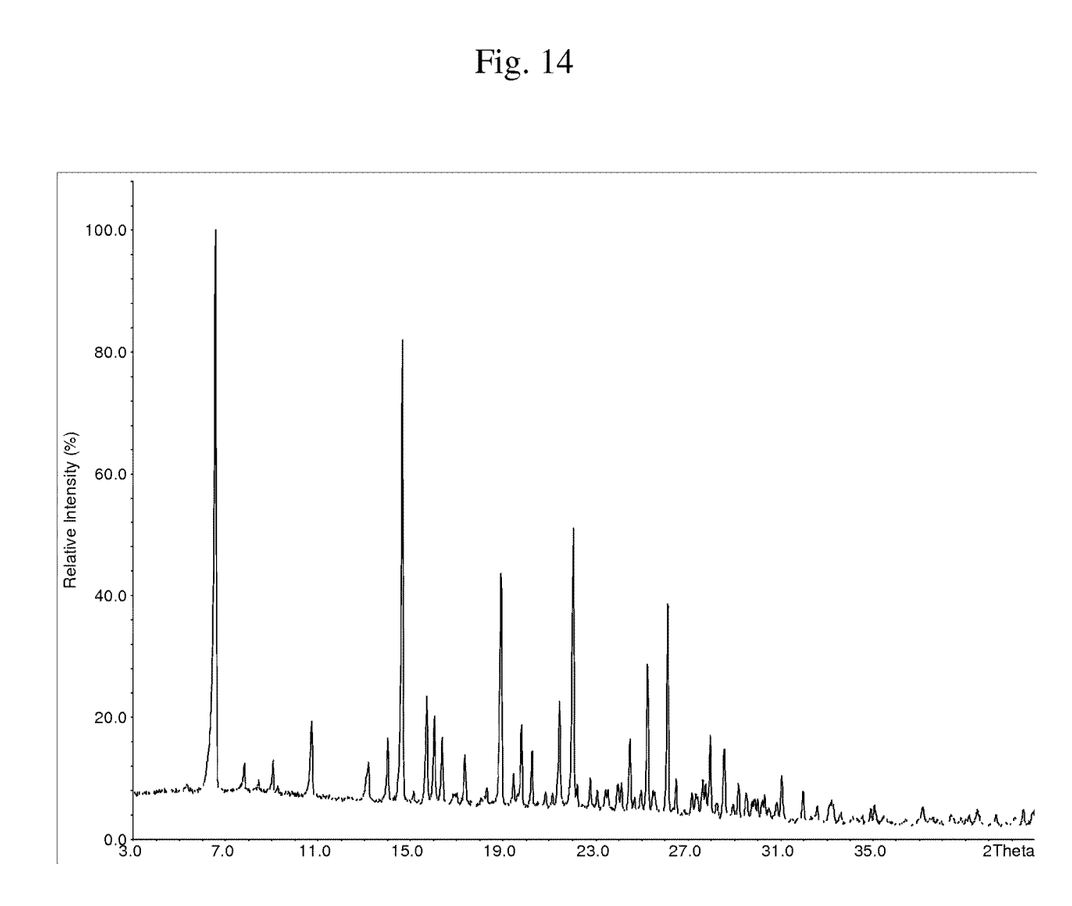
FIG. 14: XRPD curve of Form VII of compound (1)
Figure 15:
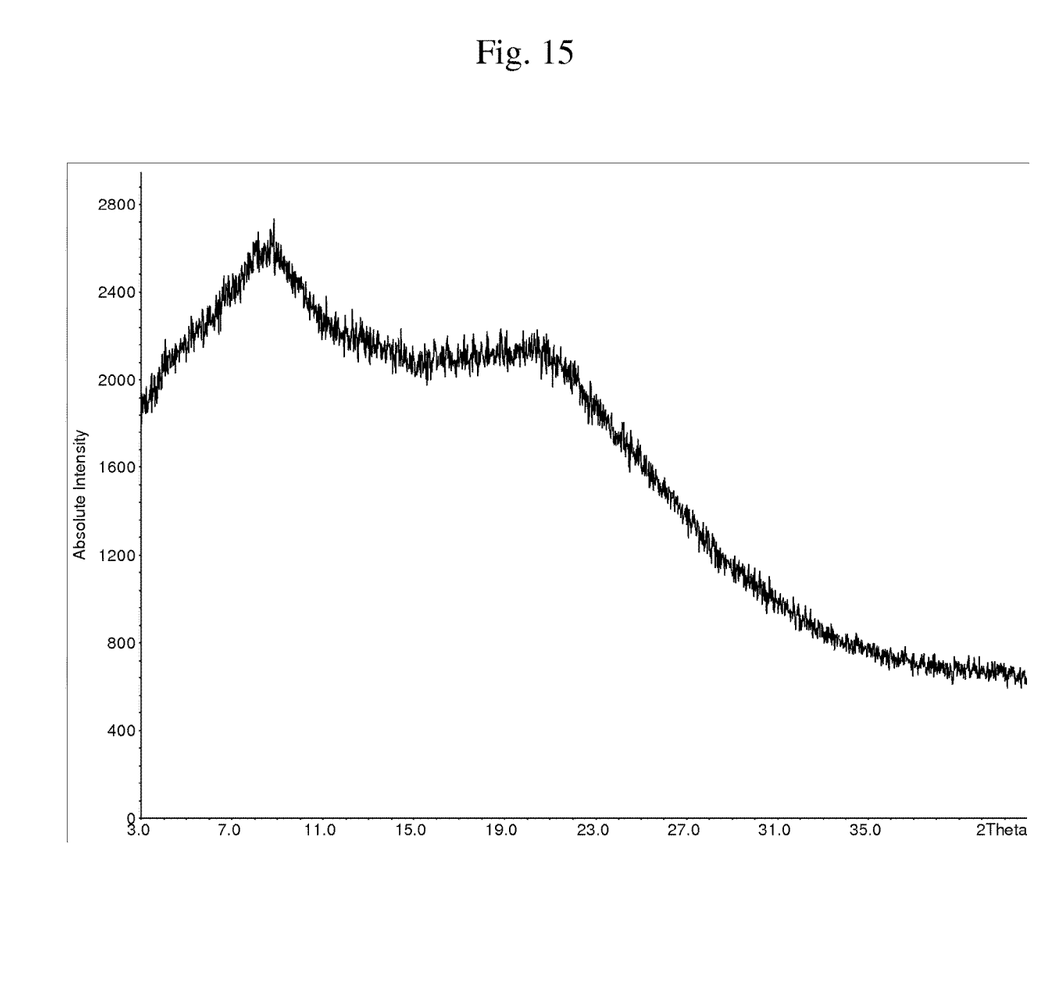
FIG. 15: XRPD curve of the amorphous form of compound (1).

In another embodiment there is provided the form VII of compound (1), characterized by the XRPD patterns at 2-theta values of 6.6, 10.7, 14.6, 15.7, 16.0, 16.4, 18.9, 19.8, 21.4, 22.0, 25.3 and 26.1; or by the corresponding characteristic wavenumbers according to Table 1.

Figure 1:
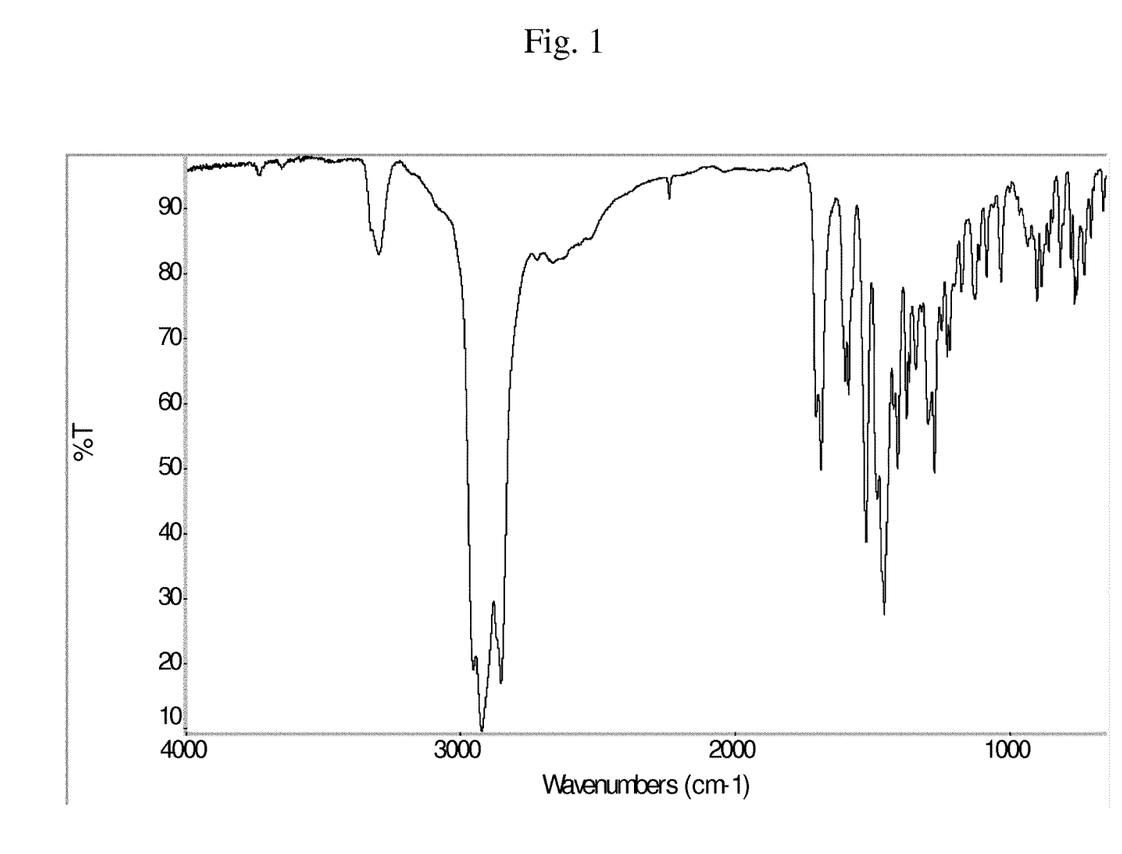
FIG. 1: FTIR spectra of amorpheous form of compound (1)

In another embodiment there is provided the amorphous form of compound (1), characterized by the FTIR wavenumbers, in $cm^{-1}$, of 1705, 1687, 1600, 1587, 1525, 1483, 1409, 1367, 1343, 1299, 1276, 1250, 1230, 1221, 1178, 1128, 1086, 1034, 902, 885, 817, 778, 765 and 729.

The solid forms of compound (1) as disclosed herein can be used in a wide variety of preparations for administration of drugs, and in particular for oral dosage forms. Exemplary dosage forms include powders or granules that can be taken orally either dry or reconstituted by addition of water to form a paste, slurry, suspension or solution; tablets, capsules, or pills. Various additives can be mixed, ground or granulated with the solid dispersion as described herein to form a material suitable for the above dosage forms. Potentially beneficial additives may fall generally into the following classes: other matrix materials or diluents, surface active agents, drug complexing agents or solubilizers, fillers, disintegrants, binders and lubricants. With respect to the solvates and polymorphs as disclosed herein, pH modifiers (e.g., acids, bases, or buffers) may also be added. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins. Examples of disintegrants include sodium starch gycolate, sodium alginate, carboxymethyl cellulose sodium, methyl cellulose, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. At least one function of inclusion of such pH modifiers is to control the dissolution rate of the drug, matrix polymer, or both, thereby controlling the local drug concentration during dissolution.

In addition to the above additives or excipients, use of any conventional materials and procedures for formulation and preparation of oral dosage forms using the compositions disclosed herein known by those skilled in the art are potentially useful. For example, the skilled artisans may formulate the compositions in an appropriate manner, and in accordance with accepted practices, such as those described in Remington's Pharmaceutical Sciences (Gennaro, Ed., Mack Publishing Co., Pa. 1990).

Consequently, a further embodiment includes a pharmaceutical preparation containing the solid forms of compound (1) as obtained by a method as described herein.

In one embodiment, there is provided a pharmaceutical composition comprising one ore several solid forms of compound (1) as disclosed herein together with pharmaceutically acceptable adjuvants or excipients.

In another embodiment, there is provided the use of one ore several solid forms as In another embodiment, there is provided the use of one ore several solid forms as disclosed herein as medicaments for the treatment of cancer, in particular AML, head and neck cancer or sarcoma.

The invention is now further described by the following specific working, which are not meant to limit in any way the scope of the present invention.

EXAMPLES

Amorphous Form 12.5 g of Compound (1) were dissolved in 487.5 g aceton and stirred at 25° C. for 1 hour. Subsequently the solution was filtered through a GF 5-filter. The clear solution was spray-dried in the Büchi Mini Spray Dryer B-290 (Inlet temperature: 90° C., Outlet temperature: 130° C., Respirator 100%, flow-rate 220 g/h. Subsequently the isolated material was dried at 50° C. under vacuum (0-20 mbar) for 24 hours.

Yield: 6.0 g (48.0%)

Form I (Polymorph)

To a solution of 15.8 g of Compound (1) in 264.2 g THF/etylacetate (70/30%-m/m) 450.0 g n-propanol were added. From the mixture 358 g solvent were distilled off (115° C. AT). The obtained suspension was cooled down to 10° C. within 5 h and hold for addition 30 mm at 10° C. The suspension was filtered and the isolated crystals were washed with 50 mL n-propanol and dried at 80° C. under vacuum (0-20 mbar) for 16 hours.

Form II (Polymorph)

A suspension of 316 mg of Compound (1) (Form I) was equilibrated in 3.0 mL of acetonitrile/water 80:20 (v/v) at ambient temperature for 25 days. The product was isolated by filtration and dried at 25° C./200 mbar for 4 days.

Form III (Polymorph)

Method A 0.5 g of Compound (1) were suspended in 5.0 g chloroform and dissolved at 60° C. The mixture was filtered through a GF 5 Filter. Subsequently the solution was cooled to room temperature and crystals were formed spontaneously. After 2 hours at room temperature, the crystals were filtered off and dried at 50° C. under vacuum (0-20 mbar) for 24 hours.

Yield: 0.2 g (40%)

Method B 20.0 g of Compound (1) were dissolved in 106.0 g tetrahydrofurane at 60° C. (AT). 300.0 g acetonitrile were added and the mixture was distilled (95° C. AT) until a volume of 300 mL was reached. The obtained suspension was cooled down to 10° C. within 1-5 h. The suspension was filtered and the isolated crystals were washed with 39.1 g acetonitrile and dried at 80° C. under vacuum (0-20 mbar) for 72 hours.

Yield: 18.8 g (94%)

Form IV (Hemi-Hydrate)

A Suspension of 2.0 g of Compound (1) in 15.8 g methanol was stirred at 25° C. for 3 days. Subsequently the white suspension was filtered and the isolated product was dried for 5 days in a vacuum oven (0-20 mbar, 50° C.) equipped with an open water bowl (to provide water vapor inside).

Yield: 1.9 g (94.0%)

Form V (Hemi-Hydrate)

200 mg of Compound (1) (Form I) were incubated in a desiccator at 75%-RH at ambient temperature for 23 days and analyzed under the same conditions.

Form VI (2-methyl THF Hemi-Solvate)

A suspension of 350 mg of Compound (1) (Form I) was agitated in 3.0 mL of 2-methyl tetrahydrofurane at ambient temperature for 28 days. The product was isolated by filtration stored at ambient conditions for 24 h.

Form VII (Acetic Acid Sesqui-Solvate)

A Suspension of 284 mg of Compound (1) (Form I) was agitated in 4.0 mL of acetic acid at ambient temperature for 26 days. The product was isolated by filtration and dried at 25° C./400 mbar for 4 days.

The invention claimed is:

1. A solid form of compound (1)

(1)

selected from
   a) a substantially amorphous form of compound (1);
   b) a hemi-hydrate, hydrate, hemi-solvate or solvate of compound (1); or
   c) a polymorph of compound (1); or
   d) a pharmaceutically acceptable salt of compound (1).

2. The solid form according to claim 1, characterized in that said solid form is a polymorph, hydrate, hemi-hydrate, solvate, hemi-solvate or pharmaceutically acceptable salt.

3. The solid form according to claim 1, characterized in that it is the amorphous form.

4. The solid form according to claim 1, characterized by the XRPD patterns at 2-theta values of 4.9, 6.9, 7.7, 9.1, 10.9, 13.5, 14.5, 17.2, 20.4, 22.3 and 25.5.

5. The solid form according to claim 1, characterized by the XRPD patterns at 2-theta values of 4.1, 5.0, 5.7, 6.3, 6.9, 7.9, 8.1, 9.0, 10.0, 14.3 and 19.5.

6. The solid form according to claim 1, characterized by the XRPD patterns at 2-theta values of 5.9, 8.3, 9.5, 10.1, 11.3, 14.2, 15.8, 17.6, 19.0, 19.4, 19.8, 20.3 and 25.5.

7. The solid form according to claim 1, characterized by the XRPD patterns at 2-theta values of 5.1, 8.0, 8.3, 8.8, 9.3, 10.0, 10.3, 13.7, 14.3, 18.7, 20.2, 20.8 and 27.6.

8. The solid form according to claim 1, characterized by the XRPD patterns at 2-theta values of 3.9, 7.8, 8.7, 9.1, 13.7, 14.5, 18.2 and 20.3.

9. The solid form according to claim 1, characterized by the XRPD patterns at 2-theta values of 5.5, 7.4, 14.5, 14.8, 15.6, 16.9, 17.8, 18.6, 19.9, 20.5, 24.8 and 26.7.

10. The solid form according to claim 1, characterized by the XRPD patterns at 2-theta values of 6.6, 10.7, 14.6, 15.7, 16.0, 16.4, 18.9, 19.8, 21.4, 22.0, 25.3 and 26.1.

11. The solid form according to claim 3, characterized by the FTIR wavenumbers, in $cm^{-1}$, of 1705, 1687, 1600, 1587, 1525, 1483, 1409, 1367, 1343, 1299, 1276, 1250, 1230, 1221, 1178, 1128, 1086, 1034, 902, 885, 817, 778, 765 and 729.

12. A pharmaceutical composition comprising one or several solid forms according to claim 1, together with pharmaceutically acceptable adjuvants or excipients.

* * * * *